US00PP32646P2

(12) United States Plant Patent
Psenner

(10) Patent No.: US PP32,646 P2
(45) Date of Patent: Dec. 15, 2020

(54) ***BIDENS* PLANT NAMED 'BID16101'**

(50) Latin Name: *Bidens ferulifolia*
Varietal Denomination: BID16101

(71) Applicant: Thomas Psenner, Bozen (IT)

(72) Inventor: Thomas Psenner, Bozen (IT)

( * ) Notice: Subject to any disclaimer, the term of this patent is extended or adjusted under 35 U.S.C. 154(b) by 0 days.

(21) Appl. No.: 16/873,436

(22) Filed: Apr. 11, 2020

(30) Foreign Application Priority Data

May 17, 2019 (CA) ..... PBR 19-9897

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Bidens* plant named 'BID16101', characterized by its low mounding and outwardly spreading to trailing plant habit; moderately vigorous to vigorous growth habit; freely branching habit; dense and bushy plant form; freely flowering habit; long flowering period; and large single-type inflorescences with bright yellow-colored ray florets.

1 Drawing Sheet

Botanical designation: *Bidens ferulifolia.*
Cultivar denomination: 'BID16101'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9897. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Bidens* plant, botanically known as *Bidens ferulifolia* and hereinafter referred to by the name 'BID16101'.

The new *Bidens* plant is a product of a planned breeding program conducted by the Inventor in Bozen, Italy. The objective of the breeding program is to create new uniformly mounding *Bidens* plants with good summer performance.

The new *Bidens* plant originated from a cross-pollination made by the Inventor in Bozen, Italy in June, 2015 of *Bidens ferulifolia* 'BID 719', disclosed in U.S. Plant Pat. No. 22,271, as the female, or seed, parent with *Bidens ferulifolia* 'BID 15054', not patented, as the male, or pollen, parent. The new *Bidens* plant was discovered and selected by the Inventor as a single flowering plant from within the progeny of the stated cross-pollination in a controlled greenhouse environment in Bozen, Italy in May, 2016.

Asexual reproduction of the new *Bidens* plant by vegetative terminal cuttings in a controlled environment in Bozen, Italy since September, 2016 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BID16101'. These characteristics in combination distinguish 'BID16101' as a new and distinct *Bidens* plant:

1. Low mounding and outwardly spreading to trailing plant habit.
2. Moderately vigorous to vigorous growth habit.
3. Freely branching habit; dense and bushy plant form.
4. Freely flowering habit.
5. Long flowering period.
6. Large single-type inflorescences with bright yellow-colored ray florets.

Plants of the new *Bidens* differ primarily from plants of the female parent, 'BID 719', in the following characteristics:

1. Plants of the new *Bidens* have larger leaves than plants of 'BID 719'.

2. Plants of the new *Bidens* have larger inflorescences than plants of 'BID 719'.

Plants of the new *Bidens* differ primarily from plants of the male parent, 'BID 15054', in the following characteristics:

1. Plants of the new *Bidens* are more trailing than and not as upright as plants of 'BID 15054'.
2. Plants of the new *Bidens* are more vigorous than plants of 'BID 15054'.
3. Plants of the new *Bidens* have larger inflorescences than plants of 'BID 15054'.

Plants of the new *Bidens* can be compared to plants of *Bidens triplinervia* X *Bidens ferulifolia* 'TOP BID 11904', disclosed in U.S. Plant Pat. No. 26,156. In side-by-side comparisons, plants of the new *Bidens* differ primarily from plants of 'TOP BID 11904' in the following characteristics:

1. Plants of the new *Bidens* have larger leaves than plants of 'TOP BID 11904'.
2. Plants of the new *Bidens* have larger inflorescences than plants of 'TOP BID 11904'.

BRIEF DESCRIPTION OF THE PHOTOGRAPHS

The accompanying colored photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

At the top of the photographic sheet (FIG. 1) is a side perspective view of a typical flowering plant of 'BID16101' grown in a container and at the bottom of the photographic sheet is a close-up view of a typical flowering plant of 'BID16101'.

DETAILED BOTANICAL DESCRIPTION

The aforementioned photographs and following observations and measurements describe plants grown during the summer in 15.25-cm containers in a polyethylene-covered greenhouse in St. Thomas, Ontario, Canada and under cultural practices typical of commercial *Bidens* production. During the production of the plants, day temperatures averaged 30° C. and night temperatures averaged 15° C. Plants were pinched when rooted cuttings were planted and were nine weeks from planting rooted cuttings when the photographs and description were taken. In the following description, color references are made to The Royal Horticultural Society Colour Chart, 2007 Edition, except where general terms of ordinary dictionary significance are used.

Botanical classification: *Bidens ferulifolia* 'BID16101'.

Parentage:

*Female, or seed, parent.*—*Bidens ferulifolia* 'BID 719', disclosed in U.S. Plant Pat. No. 22,271.

*Male, or pollen, parent.*—*Bidens ferulifolia* 'BID 15054', not patented.

Propagation:

*Type.*—By vegetative terminal cuttings.

*Time to initiate roots, summer.*—About ten days at temperatures about 18° C.

*Time to initiate roots, winter.*—About 14 days at temperatures about 18° C.

*Time to produce a rooted young plant, summer.*—About 21 days at temperatures about 18° C.

*Time to produce a rooted young plant, winter.*—About 25 days at temperatures about 18° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Low mounding and outwardly spreading to trailing plant habit; moderately vigorous to vigorous growth habit and moderate growth rate.

*Branching habit.*—Freely branching habit typically with about eight primary lateral branches each with about nine secondary lateral branches developing per plant; dense and bushy appearance.

*Plant height.*—About 19.9 cm.

*Plant diameter or spread.*—About 51 cm.

*Lateral branches.*—Length, primary branches: About 12.6 cm. Diameter, primary branches: About 3.7 mm. Internode length: About 1.9 cm. Strength: Strong, flexible. Aspect: Upright to outwardly. Texture and luster: Densely pubescent; matte. Color, developing: Close to 145B. Color, developed: Close to 144B.

Leaf description:

*Arrangement.*—Opposite, simple.

*Length.*—About 5.6 cm.

*Width.*—About 5.8 cm.

*Shape.*—Roughly deltoid, pinnatisect; three to five-lobed.

*Apex.*—Acute with mucronate tip.

*Base.*—Attenuate.

*Margin.*—Deeply dissected.

*Texture and luster, upper surface.*—Slightly pubescent; matte.

*Texture and luster, lower surface.*—Smooth, glabrous; matte.

*Venation pattern.*—Pinnate, reticulate.

*Color.*—Developing leaves, upper surface: Close to 146C. Developing leaves, lower surface: Close to 147D. Fully expanded leaves, upper surface: Close to 147B; venation, close to 144C. Fully expanded leaves, lower surface: Close to 147C to 147D; venation, close to 147C.

*Petioles.*—Length: About 1.2 cm. Diameter: About 2.4 mm. Strength: Moderately strong, flexible. Texture and luster, upper and lower surfaces: Densely pubescent; matte. Color, upper surface: Close to 144C. Color, lower surface: Close to 144B to 144C.

Inflorescence description:

*Appearance.*—Single type (daisy) solitary inflorescences developing on terminal and axillary peduncles; inflorescence form with ray and disc florets; inflorescences positioned on peduncles; inflorescences face mostly upright.

*Flowering habit.*—Freely flowering habit with more than 700 inflorescences and inflorescence buds developing during the flowering season.

*Fragrance.*—Faint, earthy.

*Flowering response.*—Early flowering habit, plants begin flowering about five to seven weeks after planting.

*Natural flowering season*.—Long flowering period, plants flower continuously from spring until frost in temperate regions and year-round in milder (above freezing) climates.

*Inflorescence longevity*.—Inflorescences last about seven days on the plant; inflorescences persistent.

*Inflorescence buds*.—Height: About 5.8 mm. Diameter: About 6.9 mm. Shape: Rounded. Texture and luster: Moderately pubescent; matte. Color: Close to 1B.

*Inflorescence size*.—Diameter: About 5.8 cm. Height: About 2.6 cm. Disc diameter: About 1.2 cm.

*Receptacles*.—Receptacle diameter: About 9 mm. Receptacle height: About 6 mm. Receptacle shape: Small, cup-shaped. Receptacle color: Close to 137C.

*Ray florets*.—Number of ray florets per inflorescence: About eight or nine arranged in a single whorl. Length: About 3.1 cm. Width: About 1.5 cm. Shape: Elliptic. Apex: Emarginate, occasionally mammillate. Base: Rounded. Margin: Entire; not undulate. Aspect: Initially upright to mostly horizontal. Texture and luster, upper and lower surfaces: Longitudinally ribbed, glabrous; matte. Color: When opening, upper surface: Close to 14A. When opening, lower surface: Close to 14B. Fully opened, upper surface: Close to 9A; venation, close to 9A; color does not change with development. Fully opened, lower surface: Close to 9A; venation, close to 150B; color does not change with development.

*Disc florets*.—Number of disc florets per inflorescence: About 78 in about five to six whorls at the center of the receptacle. Length: About 8 mm. Diameter: Less than 1 mm. Shape: Tubular, slender; apex, five-pointed. Texture and luster: Smooth, glabrous; slightly glossy. Color: When opening, inner and outer surfaces: Close to 153D and at the base, close to 1D. Fully opened, inner and outer surfaces: Close to 153D and at the base, close to 1D.

*Phyllaries*.—Quantity per inflorescence: About ten to twelve arranged in about two whorls. Length: About 8 mm. Width: About 2 mm. Shape: Linear. Apex: Acute. Base: Truncate. Margin: Entire. Texture and luster, upper and lower surfaces: Slightly pubescent; matte. Color, upper and lower surfaces: Close to 137B.

*Peduncles*.—Length, terminal peduncle: About 5.5 cm. Length, third peduncle: About 7.6 cm. Diameter: About 1 mm. Strength: Strong; flexible. Aspect: Terminal peduncles, mostly erect; axillary peduncles, about 45° from vertical. Texture and luster: Densely pubescent; matte. Color: Close to 145B tinged with close to N77C.

*Reproductive organs*.—Androecium: Present on disc florets only. Quantity per disc floret: Five. Filament length: About 6 mm. Filament color: Close to 145B. Anther size: About 1 mm by 2 mm. Anther shape: Ellipsoidal. Anther color: Close to 200A. Pollen amount: Scarce. Pollen color: Close to 21A. Gynoecium: Present on disc and ray florets. Quantity per floret: One. Pistil length: About 7 mm. Style length: About 5 mm. Style color: Close to 14B. Stigma diameter: Less than 1 mm. Stigma shape: Bi-parted. Stigma color: Close to 14A. Ovary color: Close to 144D.

*Seeds and fruits*.—To date, seed and fruit development have not been observed on plants of the new *Bidens*.

Pathogen & pest resistance: To date, plants of the new *Bidens* have not been shown to be resistant to pathogens and pests common to *Bidens* plants.

Garden performance: Plants of the new *Bidens* have been observed to have good garden performance and to tolerate temperatures from about 2° C. to about 40° C. and are suitable for USDA Hardiness Zones 9 and 11.

It is claimed:

1. A new and distinct *Bidens* plant named 'BID16101' as illustrated and described.

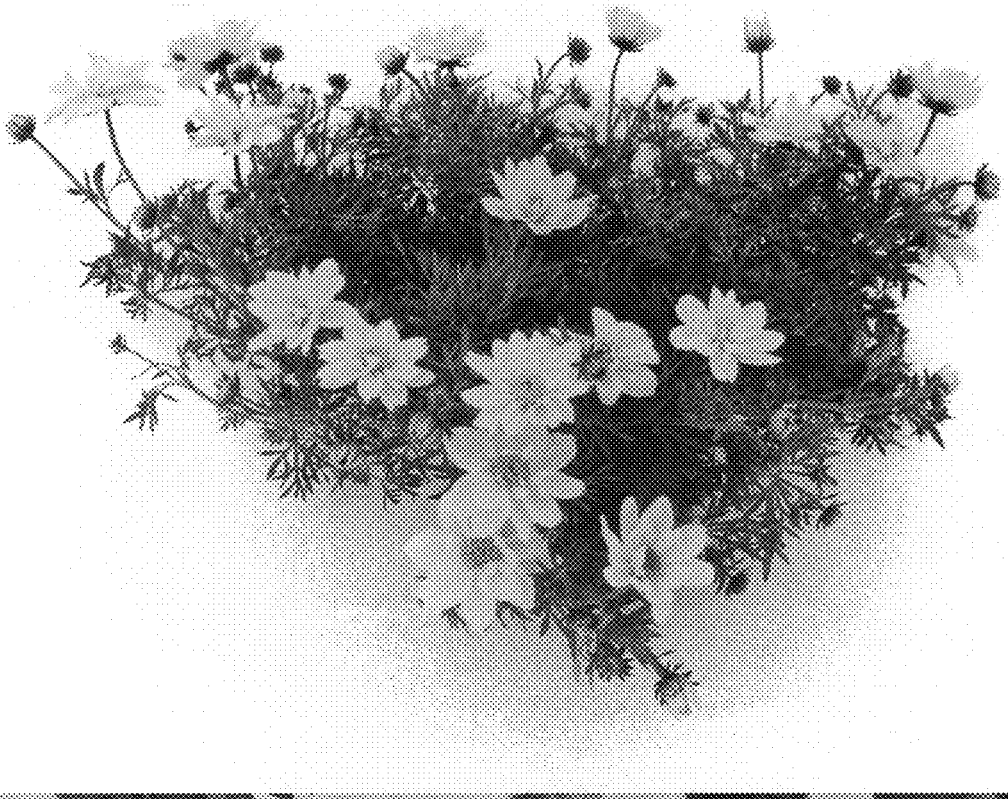
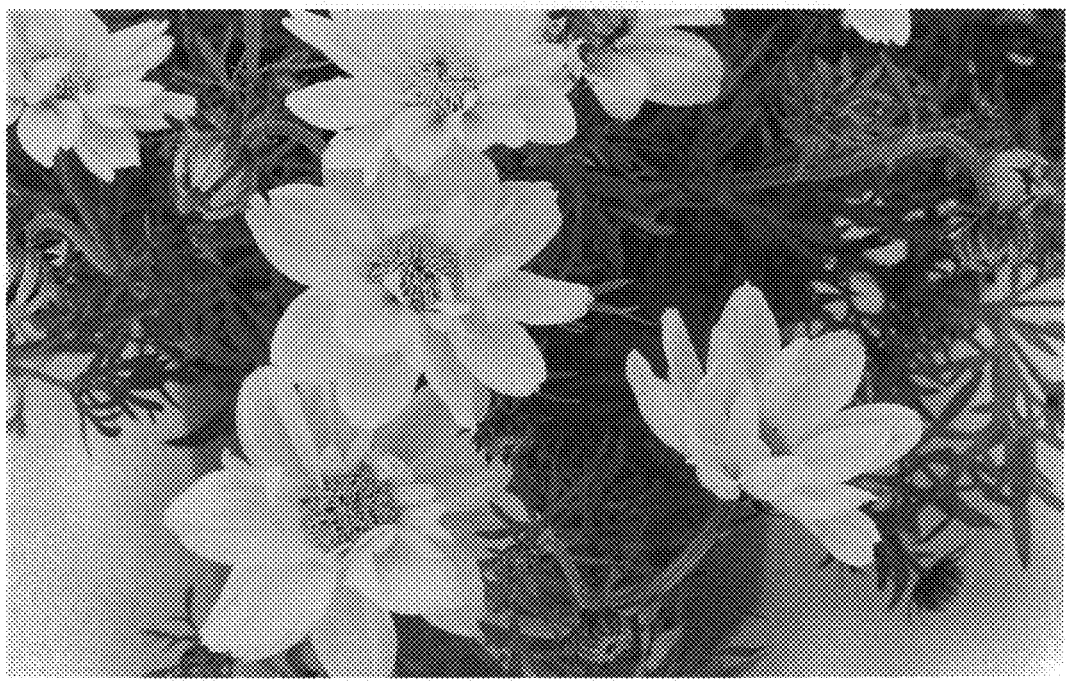

* * * * *